United States Patent [19]
Vigilia

[11] Patent Number: 4,881,540
[45] Date of Patent: Nov. 21, 1989

[54] DEVICE AND METHOD FOR ASSISTING IN ARTIFICIAL RESPIRATION

[76] Inventor: Larry P. Vigilia, 341 Harvey Dr., #1, Glendale, Calif. 91206

[21] Appl. No.: 152,651

[22] Filed: Feb. 5, 1988

[51] Int. Cl.[4] .............................................. A61M 16/00
[52] U.S. Cl. ........................... 128/202.28; 128/202.29; 128/203.11; 128/205.13
[58] Field of Search ....................... 128/202.28, 202.29, 128/203.11, 207.14

[56] References Cited

U.S. PATENT DOCUMENTS

| | | | |
|---|---|---|---|
| 3,013,554 | 12/1961 | Safar et al. | 128/202.28 |
| 3,068,590 | 12/1962 | Padellford | 128/202.28 |
| 3,089,485 | 5/1963 | Hirschhorn | 128/202.28 |
| 3,106,916 | 10/1963 | Matthes | 128/202.28 |
| 3,242,921 | 3/1966 | Seeler | 128/203.11 |
| 4,030,493 | 6/1977 | Walters et al. | 128/207.14 |
| 4,360,017 | 11/1982 | Barlett | 128/202.28 |
| 4,462,400 | 7/1984 | Simons et al. | 128/207.14 |
| 4,676,240 | 6/1987 | Gardy | 128/207.14 |
| 4,697,587 | 10/1987 | Marinkovich | 128/203.11 |

*Primary Examiner*—Edgar S. Burr
*Assistant Examiner*—Kimberly L. Asher

[57] ABSTRACT

A device and method are set forth to assist in providing artificial respiration and at the same time avoid intimate contact. Included is a conduit defining an airway with an outwardly projecting flange portion to be received in the person's mouth and seal against the inside surface of the lips about the mouth opening. A check valve prevents reverse flow of air through the device. The device may be adapted to also define a tongue depressor. The person providing artificial respiration blows through the device to supply respiring air to the person receiving the same.

7 Claims, 2 Drawing Sheets

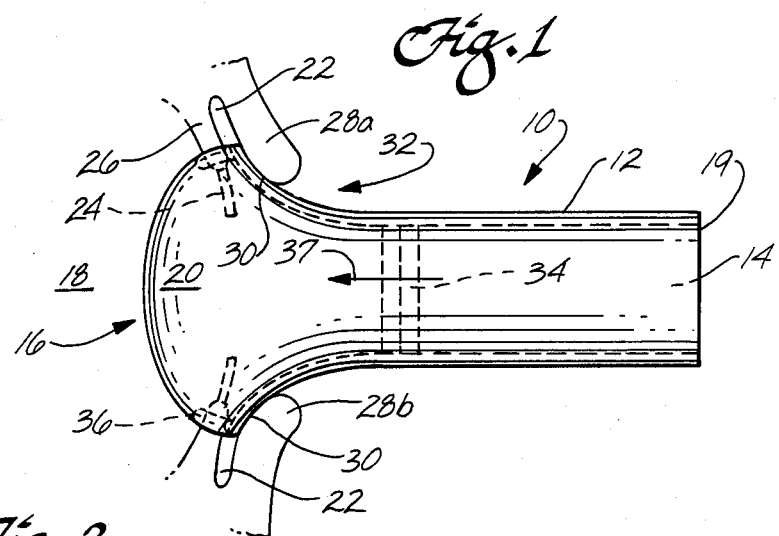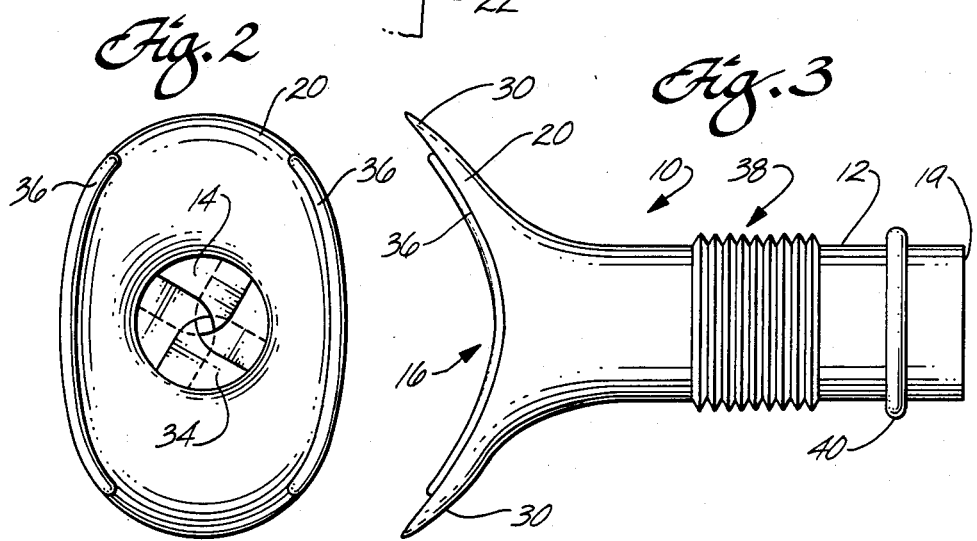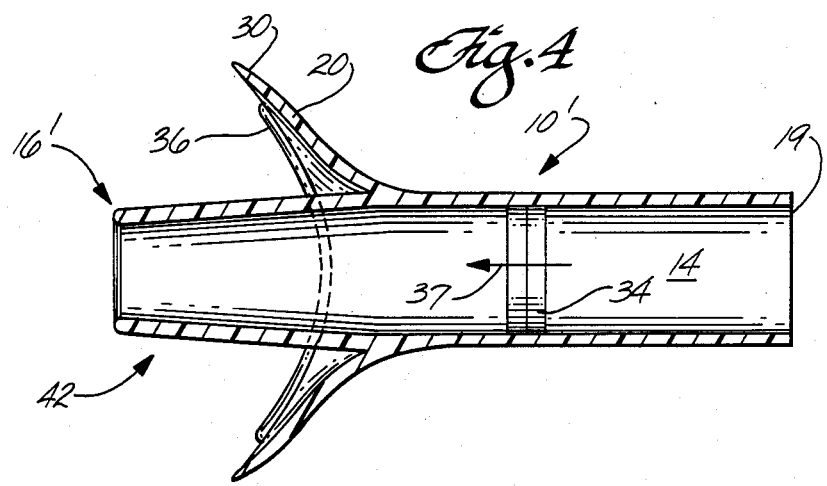

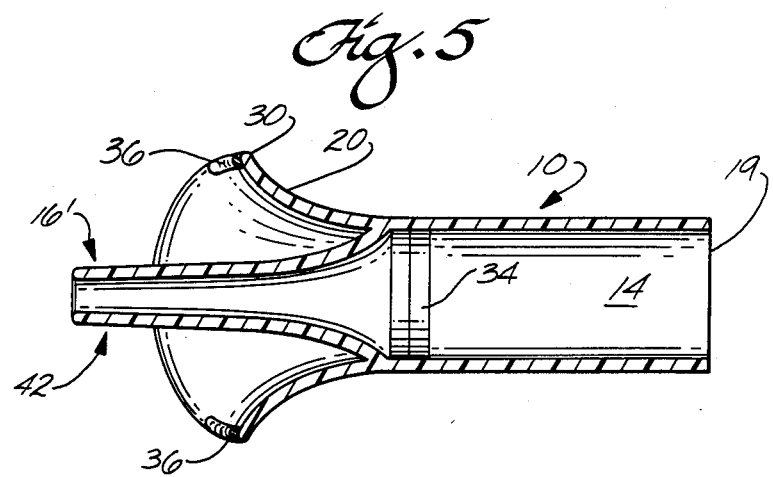

DEVICE AND METHOD FOR ASSISTING IN ARTIFICIAL RESPIRATION

FIELD OF THE INVENTION

This invention relates to devices for assisting in providing artificial respiration. More particularly, it relates to devices and methods to assist in providing artificial respiration without requiring mouth-to-mouth contact between persons.

BACKGROUND OF THE INVENTION

Artificial respiration has long been recognized as a method whereby one person can induce another, having stopped breathing, to respire. Heretofore, artificial respiration has included putting the person to receive artificial respiration on their back and tilting their head back to open the air passage to the lungs. Making sure the tongue is not obstructing the air passage, the person's nostrils are closed and the respiring person places his/her mouth over that of the person receiving artificial respiration and respiring air is blown into the person's mouth and lungs. Pulling back, the respiring air is exhaled from the lungs and mouth. This process is repeated until, for example, emergency assistance arrives.

If available, a person can artificially respire using a mouth and nose covering mask and a collapsible bag. Holding the mask over the person's nose and mouth the bag is collapsed and released to provide artificial respiration.

With diseases such as herpes, syphilis, acquired immunodeficiency syndrome (AIDS) and others, reluctance has been expressed by some to render artificial respiration. This is true since one must make intimate, mouth-to-mouth contact with the person who is to receive artificial respiration. Even if a bag respirator is available, it is often difficult to obtain a good seal about the nose and mouth for a proper respiration.

Hence, a need is seen for an inexpensive, efficient and compact device to assist in providing artificial respiration.

SUMMARY OF THE INVENTION

There is, therefore, provided according to the present invention, a device and method for assisting and providing artificial respiration which eliminates the need for mouth-to-mouth contact between the person delivering respiring air and the person receiving the same and which provides a seal for efficient transmission of respiring air.

Towards this end, the device is to assist in providing artificial respiration to a person according to the present invention includes a conduit defining an airway to pass air from the person providing respiring air to the person receiving the same. The conduit has a first end received into the mouth of the person receiving the respiring air and an open second end to be received into the mouth of the person providing the same. A flange portion extending outwardly from the conduit is contoured and adapted to be received into the person's mouth between the gums and lips and to define a surface adapted to seal the device against the inside surface of the person's lips. Means are provided for preventing the reverse flow of air from the respired to the respiring person through the conduit.

In order to define the flange and surface described hereinabove, said flange may be semicylindrical or semispherical with a smooth surface to mate with the inside surface of the person's lips. Means may be provided for resiliently urging the flange forwardly from the gums to assure the mating seal between the surface and lips.

In a further embodiment, the conduit first end may be fashioned to define a tongue depressor to hold the tongue in such a manner as to not block the air passage.

Also set forth, according to the present invention, is a method for providing artificial respiration to a person which comprises inserting a respiration assisting device into the mouth of the person being respired, the device having a conduit defining an airway to pass air from the respiring person into the mouth and windpipe of the respired person, the conduit having a first end to be received into the respired person's mouth and an open second end to receive the respiring air. The device further includes a flange portion extending outwardly to be received into the respired person's mouth between the gums and lips and defining a surface adapted to seal the device against the inside surface of the lips about the mouth opening and further includes means for preventing the reverse flow of air through the conduit. The method further includes closing the respired person's nostrils and blowing respiring air into the conduit and therethrough and into the respired person's mouth and lungs. Further, the method includes allowing the respired person's nostrils to open to permit the person to exhale.

As can be appreciated, the device and method according to the present invention dispenses with the need for intimate, mouth-to-mouth contact between the respiring and respired person thereby relieving a concern of transmission of disease. Also air is prevented from flowing into the mouth of the respiring person further relieving concern about the transmission of disease. Additionally, it is believed that the seal defined between the flange surface and lips defines a more efficient seal that is provided by other devices such as the mask used with the respiring bag. As still a further feature, the device and method according to the present invention helps in providing artificial respiration by even those who are unfamiliar with the procedure.

BRIEF DESCRIPTION OF THE DRAWINGS

These and other features and advantages of the present invention will become appreciated as the same becomes better understood with reference to the specification, claims and drawings wherein:

FIG. 1 is a side view of one embodiment of the device according to the present invention shown positioned in the respired person's mouth;

FIG. 2 is an end view of the first end of the device of FIG. 1;

FIG. 3 is a top view of a further embodiment of the device according to the present invention;

FIG. 4 is a plan view of still a further embodiment of the device according to the present invention; and FIG. 5 is a side section view of the device of FIG. 4.

DETAILED DESCRIPTION

Turning to FIG. 1, one embodiment of device 10 according to the present invention is shown. Device 10 includes a conduit 12 which may be circular in cross-section or any other suitable shape and any desired length and fashioned from any desired material. Conduit 12 defines an airway 14 through which respiring air will pass from the person providing artificial respiration (respiring person) to the person receiving the same (respired person). Conduit 12 has a first end 16 adapted to be received into the mouth 18 of the respired person and a second end 19 upon which the respiring person places his/her mouth. Device 10 further includes a flange 20 which as shown in FIG. 1 is received through mouth opening 32 and into the mouth 18 of the respired person and is adapted to be located in the space or pocket 22 defined between the teeth 24 and gums 26 and upper and lower lips 28a and 28b. For this purpose, flange 20 may be semicylindrical or semispherical and, as shown in FIG. 2, have an overall oval profile in end view. Accordingly, with the device 10 thusly inserted into mouth 18 of the respired person, flange 20 nests in pockets 22 holding device 10 in position.

To provide a seal for the device 10, flange 20 or at least the margin thereof, defines a surface 30 which is adapted to mate with the inside surface of the upper and lower lips 28a, 28b and the entire area inside mouth 18 about mouth opening 32. Surface 30 may be smooth to so mate with the inside of the lips about the mouth opening 32 providing a surface-to-surface seal. With the saliva present, the seal between surface 30 and the inside of the mouth opening 32 is enhanced.

To prevent reverse flow of respiring air, which would also raise concerns regarding the transmission of disease, the device 10 further includes means for preventing the reverse flow of air through airway 14. As illustrated in FIGS. 1 and 2, these means may be embodied as a flapper-type check valve 34 disposed in conduit 12. Check valve 34 is adapted to permit the flow of respiring air in only the direction of arrow 37 rough airway 14 and into mouth 18 of the respired person.

Accordingly, to provide artificial respiration with device 10, the respired person is placed on his/her back and his/her mouth is opened such that the first end 16 of device 10 is inserted through mouth opening 32 to locate the flange 20 in pockets 22 and generally within and about the inside of mouth opening 32. In this position, device 10 is retained by so locating the flange and a seal is defined between flange surface 30 and the inside surfaces of the lips about mouth opening 32. Flange 20 interacts with pockets 22 to retain the mouth 18 open as shown in FIG. 1. Saliva within mouth 18 enhances the aforementioned seal; alternatively, surface 30 may be appropriately coated with a viscous or otherwise sealing material for enhancing the seal. Thereafter, the respiring person closes the nostrils of the person being respired with, for example, the thumb and forefinger of the right hand and thereafter blows through the second end 19 into airway 14 through check valve 34 and into mouth 18 and lungs of the person being respired. Thereafter, the person releases the nostrils permitting the respired person to exhale through their nose and repeats the process as required until breathing is restored or help arrives.

As can be appreciated, by using device 10, the respiring person need not make mouth-to-mouth contact with the person being respired and therefore need not be concerned about contracting disease. Further, there is no passing of air from the respired person to the respiring person.

Turning to FIG. 2, an additional feature according to the present invention is shown. To secure the seal between surface 30 and the lips about mouth opening 32, flange 20 may include means for urging flange 24 forwardly of teeth or gums 24, 26. These means may include protuberances 36 which are adapted to come in contact with gums 26 or teeth 24 and to urge the flange 24 forwardly to assure that surface 30 makes a sealing and mating contact with the inside of the lips about mouth opening 32. Protuberances 36 may be constructed of resilient material.

With reference to FIG. 3, device 10 may further be fashioned to include an accordion like segment 38 of conduit 12 about which conduit 12 may be flexed, extended or collapsed. An additional feature includes a peripheral ring 40 about conduit 12 adjacent second end 19 providing a gripping surface for holding device 10 during positioning and artificial respiration.

With reference to FIGS. 4 and 5, still further embodiments of a device according to the present invention is shown. Like parts carry like reference numbers.

Device 10' according to this embodiment has a first end 16' which is generally tapered as best shown in FIG. 5 to define a tongue depressor 42. Conduit 12 may reduce down to define tongue depressor 42, as shown in FIG. 5, or tongue depressor 42 may be incorporated as a separate component affixed within conduit 12. Airway 14 extends from second end 19 through conduit 12 and tongue depressor 42 to pass air through device 10'. Accordingly, when device 10' is inserted through mouth opening 32, tongue depressor 42 is located to depress the respirated person's tongue and assure that the tongue does not close the air passage during respiration. Of course, while tongue depressor 42 is shown as being rectangular in cross section, it can have any suitable shape. Additionally, tongue depressor 42 may, instead of defining a duct or airway, may simply be a tongue depressing surface extending from device 10'.

The device hereinabove described may be constructed from plastic or any other suitable material and may be made flexible or collapsible. Further the conduit second end 19 may be adapted to be coupled with a collapsable bag of the type used to provide artificial respiration. Accordingly upon arrival of medical assistance or even at a medical care facility the device and collapsible bag may be used.

While I have shown and described certain embodiments of the present invention, it is to be understood that it is subject to modifications without departing from the spirit and scope thereof.

What is claimed is:

1. A device to assist in providing artificial respiration to a person comprising:
   a conduit defining an airway to pass air into the mouth and lungs of the person, said conduit having a first end to be received in the person's mouth and an open second end to receive respiring air;
   a flange portion extending outwardly from the conduit to be received into the person's mouth between the gums and lips, said flange portion defining a surface adapted to seal the device against the inside surface of the lips about the mouth,
   means to induce a seal between the flange and the inside of a person's lips without conscious cooperation of the person, said means including means for urging the flange portion against the inside surface of the lips, and
   means for preventing reverse flow of air from said person through the conduit.

2. The device of claim 1 wherein the urging means includes a spacing protuberance extending from said flange against the person's gums.

3. The device of claim 2 wherein the protuberance is resilient.

4. The device of claim 1 wherein the conduit first end is also adapted to act as a tongue depressor.

5. The device of claim 4 wherein the conduit first end narrows convergingly to define a tongue depressing surface.

6. The device of claim 1 wherein said conduit is flexible.

7. A method for providing artificial respiration to a person comprising:

providing a respiration assisting device for insertion into the mouth of the person receiving artificial respiration, the device having a conduit defining an airway to pass air into the mouth and windpipe of the person, said conduit having a first end to be received in the person's mouth and an open second end to receive respiring air, a flange portion extending outwardly from the conduit to be received into the person's mouth between the gums and lips, said flange portion defining a surface adapted to seal the device against the inside surface of the lips, means to induce a seal between the flange and the inside of a person's lips without conscious cooperation of the person, said means including means for urging the flange portion against the inside surface of the lips, and means for preventing reverse flow of air from said person through the conduit;

inserting said respiration assisting device into the mouth of a person;

closing the person's nostrils while blowing respiring air into the conduit second end and through the conduit and airway into the person's mouth and lungs; and allowing the nostrils to open to permit the person to exhale.

* * * * *